United States Patent [19]

Alföldi et al.

[11] 4,294,927

[45] Oct. 13, 1981

[54] GENETIC PROCESS FOR THE PREPARATION OF ANTIBIOTIC-PRODUCER MICROMONOSPORA STRAINS

[75] Inventors: Lajos Alföldi; Katalin Bálint née Fodor; Csaba Kari; István Török, all of Szeged; György Szvoboda, Budapest; Tibor Láng, Budapest; István Gádo, Budapest; Gábor Ambrus, Budapest, all of Hungary

[73] Assignee: Gyogyszerkutato Intezet, Budapest, Hungary

[21] Appl. No.: 92,554

[22] Filed: Nov. 8, 1979

[30] Foreign Application Priority Data

Nov. 13, 1978 [HU] Hungary .................... GO 1430

[51] Int. Cl.$^3$ ............................................. C12N 15/00
[52] U.S. Cl. .................................. 435/172; 435/80; 435/867; 435/869
[58] Field of Search ......................................... 435/172

[56] References Cited
PUBLICATIONS

Hopwood et al., Nature, vol. 268, pp. 171–174.

Baltz, Journal of General Microbiology, vol. 107, pp. 93–102 (1978).

Beretta et al., Journal of Bacteriology, vol. 107, pp. 415–419 (1971).

*Primary Examiner*—Alvin E. Tanenholtz
*Attorney, Agent, or Firm*—Young & Thompson

[57] ABSTRACT

The invention provides a process for the preparation of antibiotic-producer Micromonospora strains having modified genetic material, wherein a protoplast suspension is prepared with lysozyme, under osmotically buffered conditions ensured by sucose, from each culture of the two genetically marked mutants of the antibiotic-producer Micromonospora strain following cultivation in a glycine medium, both suspensions obtained are combined in the presence of polyethylene glycol, and incubated at room temperature, the resulting fused protoplasts are suspended in soft agar, then plated on an agar plate containing sucrose, prolin and inorganic salts, incubated for 20 to 30 days, and finally all mutants are selected from the regenerated colonies which are sure to have genetic material different from that of the parent strains.

The process can be advantageously applied to improve productivity of antibiotic-producer strains having industrial importance.

9 Claims, No Drawings

GENETIC PROCESS FOR THE PREPARATION OF ANTIBIOTIC-PRODUCER MICROMONOSPORA STRAINS

The invention relates to a novel process for the preparation of antibiotic-producer Micromonospora strains having modified genetic material.

It is widely known that antibiotic production is a genetically determined property. Consequently any change induced in the genetic material of a producer strain may alter its antibiotic-producing property, too. These stable genetic changes (mutations) occur also spontaneously, though very rarely. The incidence of mutations may be enhanced by known methods, i.e. UV, near-UV, gamma and x-ray irradiations as well as treatment with different mutagenic agents. These methods have been successfully applied at a variety of strains to enhance their antibiotic-producing capacity. It is a severe drawback of these methods that the mutation induced is a random process, cannot be controlled, and that not all survivors of the mutagenic treatment become mutants. So a large number of survivors has to be screened in order to obtain finally a better producer mutant.

It is known that several enzyme levels are raised by enhancing the gene dose, i.e. if the gene is doubled within a given chromosome, the level of the protein coded by it is doubled, too. Similarly, the synthesis of antibiotics may be increased by raising the level of enzymes responsible for antibiotic synthesis. The mechanism of gene duplication has not been elucidated yet, nor is it known which of the mutagenic agents is primarily inducing gene duplication.

It can be concluded that any process able to increase significantly the number of gene duplications may be of major importance in augmenting the productivity of antibiotic-producer strains.

Considering industrial applications, a new species can be prepared from two Micromonospora strains producing antibiotics of related structure, which has more advantageous properties both as regards cultivation or yield, or which can produce a novel valuable antibiotic having a similar structure to the antibiotics formed by the parent strains.

The process of protoplast fusion may be the method of choice to solve the above problems.

It is the objective of the present invention to advantageously modify the genetic properties of Micromonospora strains by means of recombination.

Except for one paper (Beretta et al., J. Bact., 107, 415 /1971/) no method is described for the genetic information transfer in the Micromonospora genus having industrial importance. Compared to the incidence of recombinations ($10^{-6}$) described in Streptomycetes, in Micromonospora no recombinations could be attained by any of the conventional methods while the protoplast fusion method developed could achieve genetic information transfer with a frequency of $10^{-3}-10^{-4}$.

In the course of protoplast fusion the entire cytoplasm of two or more protoplasts, consequently their complete genetic material, is unified. The selection performed thereafter furnished either stable merodiploids or recombinants. With merodiploids the number of genes responsible for antibiotic synthesis may be enhanced within the cell even if the selection is not carried out with the objective of augmenting antibiotic production. Gene duplication may occur also in the course of recombinations. It is a further advantage of the method that in the course of protoplast fusion large chromosome fragments, transferred from the donor into the recipient, are fixed with a higher incidence in the colonies surviving selection than with any other method applied till now in bacterial genetics.

The protoplast fusion method has been widely applied for studying the genetic properties of both mammal and plant cells as well as those of fungi.

Due to difficulties in cell wall regeneration the first papers published about bacterial protoplast fusion appeared around 1976 (K. Fodor and L. Alföldi, Proc. Natl. Acad. Sci. U.S.A. 73, 2147 /1976/; P. Schaeffer et al., Proc. Natl. Acad. Sci. U.S.A. 73, 2151 /1976/; D. A. Hopwood et al., Nature 268, 171 /1977/; R. H. Baltz, J. Gen. Microbiol., 107, 93 /1978/; O. Godfrey et al., Can. J. Microbiol., 24, 994 /1978/).

No paper was ever published about protoplast fusion in the Micromonospora genus.

Accordingly, the present invention provides a process for the preparation of antibiotic-producer Micromonospora strains having modified genetic material, wherein following cultivation in a glycine medium, a protoplast suspension is prepared with lysozyme, under osmotically buffered conditions ensured by sucrose, from each culture of the two genetically labelled mutants of the antibiotic-producer Micromonospora, the two suspensions obtained are combined in the presence of polyethylene glycol, and incubated at room temperature. The resulting fused protoplasts are suspended in soft agar, then plated on an agar plate containing proline and inorganic salts, incubated for 20 to 30 days, and finally all mutants are selected from the regenerated colonies which are sure to have genetic material different from that of the parent strains.

To promote the lysis of the cell wall by means of lysozyme, glycine (0.2 to 0.5 percent) is preferably added to the culture medium. Due to the inhibitory effect exerted by glycine on cell wall synthesis, it is a common feature of these glycine-sensitized cultures that mycelial hyphae are both shorter and thicker compared to those grown in the absence of glycine, and in addition bulges appear on them. Only cultures showing similar microscopic picture can yield protoplast suspensions with satisfactory efficacy.

These sensitized cultures are treated for 30 to 90 minutes with lysozyme (5–10 mg/ml) under osmotically buffered conditions (in a medium containing preferably 0.2–0.35 M sucrose).

Combining the individual protoplast suspensions prepared from various mutants at a ratio of 1:1, and treating the mixture with polyethylene glycol (m.w. 6000) the protoplasts undergo fusion. The suspension containing the fused protoplasts is incubated in a regenerating agar under osmotically buffered conditions ensured by sucrose, and proline as well as inorganic salts, preferably $CaCl_2$, $MgCl_2$ and $KH_2PO_4$, promoting regeneration, in a temperature range of 30° to 37° C. The protoplasts are regenerated within 20 to 30 days.

The genetic properties of each parent pair chosen should ensure the successful selection of recombinants formed in the course of fusion. For this purpose antibiotic resistance or various auxotrophs may be applied which were already used with success in conventional microbial genetics.

In accordance with the present invention in the case of the sisomicin-producer *Micromonospora inyoensis* ATCC 27600 a casamino acid dependent but rifampicin resistant, and a casamino acid non-dependent but rifampicin sensitive (sensitive already to 0.5 μg/ml of rifampicin) parent pair was utilized. Following completed fusion mutants were looked for which are non-dependent on casamino acid for growth but are rifampicin resistant, i.e. are forming colonies in minimal medium containing 10 μg/ml of rifampicin. Regeneration is carried out in non-selective medium ensuring optimal conditions for regeneration. In order to select recombinant phenotypes, the regenerated colonies are washed off, and the suspension obtained is plated onto a minimal medium containing 10 μg/ml of rifampicin. The colonies formed from individual cells having recombinant phenotypes are obtained as a result of fusion.

According to a further advantageous method of execution of the process of the invention a novel selecting process is used whereby the protoplasts of one of the parents are inactivated by heat treatment. The heat treatment should be effective enough to ensure loss of viability, at the same time should be mild enough to preserve the genetic material intact. In this case the complete genetic material of one partner is transferred into the heat-inactivated cytoplasm of the other partner. This procedure provides a means for selection when only one of the parents is marked genetically.

This principle was used for the gentamicin-producer *Micromonospora purpurea* var. nigrescens (MNG 00122) strain by applying a streptomycin-resistant-streptomycin-sensitive parent pair. For the selection of recombinants the protoplasts of the resistant parent were cautiously heat-inactivated (55° C.) prior to fusion. As streptomycin sensitivity is a dominant feature over streptomycin resistance, 8 to 10 days have to elapse prior to the selection of recombinants (phenotype lag). After 8 to 10 days 10,000 μg/ml of streptomycin is layered on the regeneration plates. The genetic material of the colonies formed after 20 to 30 days is different from that of the parent pairs.

Applying heat inactivating techniques and utilizing the fact that *Micromonospora purpurea* var. nigrescens is more resistant to streptomycin by two orders of magnitude than *Micromonospora inyoensis*, the interspecific hybride of the two strains is prepared by protoplast fusion. According to this procedure the protoplast suspension of streptomycin-resistant *Micromonospora purpurea* var. nigrescens is heat-inactivated and fused with the protoplast suspension of streptomycin-sensitive *Micromonospora inyoensis*. After 8 to 10 days agar containing 1000 μg/ml of streptomycin is layered on the fused protoplasts to be regenerated. The colonies formed after 20 to 30 days are interspecific hybrides.

The above principle was also applied for parent pairs bearing other genetic marking. One parent is casamino-acid dependent while the other is non-dependent. For the selection of recombinants the protoplasts of the casamino-acid dependent parent are cautiously heat-inactivated. The fused protoplasts are layered on minimal agar. The colonies formed after 20 to 30 days have recombinant properties.

In studies investigating the antibiotic-producing property of strains having genetic material modified by the process of the present invention, methods described in the literature are used. Thus for instance, in studying the antibiotic production of recombinants prepared from the gentamicin-producer *Micromonospora purpurea* var. nigrescens (MNG 00122), the strain is grown under conditions optimized for antibiotic production (I. Gado et al., Hungarian Pat. No. 168,778 /1973/). The microbiological activity of the fermentation broth is determined by agar diffusion assay applying *Staphylococcus epidermidis* as test organism, and the composition of the gentamicin biosynthesized is assayed according to the procedure described in the Federal Register (21. Food and Drugs, Apr. 1, 1977, 444.20 a/b, pp. 433 to 435).

It was found that the protoplast fusion process is suitable for the transfer of genetic information into other aminoglycoside-producing Micromonospora, too, at a fairly high frequency. In addition studies were carried out with the following strains:
*Micromonospora olivoasterospora*,
*Micromonospora echinospora*,
*Micromonospora purpurea* (holotype).

The process of the invention is further illustrated by the aid of the following non-limiting Examples.

EXAMPLE 1

The deep-freezed, vegetative mycelium of the following two mutants of sisomicin-producer *Micromonospora inyoensis* ATCC 27600:
1. casamino-acid dependent, rifampicin-resistant $Cas^-$ $Rif^R$, and
2. casamino-acid non-dependent, rifampicin-sensitive $Cas^+Rif^S$ each is inoculated under sterile conditions into 500 ml Erlenmeyer flasks containing each 100 ml of a sterile seed medium consisting of
1%: soymeal,
1%: potato starch,
1%: sucrose
0.4%: $CaCO_3$
suspended in tap water.

The seed medium inoculated with $Cas^-Rif^R$ is incubated for 40 hours at 37° C. on a rotary shaker. Then this seed medium is inoculated under sterile conditions into a 500 ml Erlenmeyer flask containing 100 ml of a sterile medium having the following composition:
0.1%: $KNO_3$
0.05%: $K_2HPO_4$
0.05%: $MgSO_4.7H_2O$
0.05%: NaCl
1.0%: glucose
0.1%: yeast extract
0.3%: casamino acid
0.2%: glycine
in distilled water.

Following inoculation this culture is incubated in this medium for 48 hours at 37° C. on a rotary shaker.

The seed medium inoculated with $Cas^+Rif^S$ is incubated for 65 hours at 37° C. on a rotary shaker, then this seed medium is inoculated under sterile conditions into 500 ml Erlenmeyer flasks each containing 100 ml of sterile medium having the following composition:
0.1%: $KNO_3$
0.05%: $K_2HPO_4$
0.05%: $MgSO_4.7H_2O$
0.05%: NaCl
1.0%: glucose
0.1%: yeast extract
0.5%: glycine
dissolved in distilled water.

Following inoculation this culture is incubated in this medium for 23 hours at 37° C. on a rotary shaker.

The culture of both mutants is centrifuged (6000 r.p.m.), the supernatant is discarded and the residue resuspended in 20 ml of medium $P_1$ consisting of 0.2 M: sucrose
0.25 g/l: $K_2SO_4$
0.025 M: TRIS-HCl+ buffer, pH 7.2
50 mM: $MgCl_2$
10 mM: $CaCl_2$
0.8 mM: $K_2HPO_4$
2 ml/l: solution of trace elements
dissolved in distilled water.
(+TRIS=tris/hydroxymethyl/-aminomethane)

Composition of the solution containing trace elements:
40 mg/l: $ZnCl_2$
200 mg/l: $FeCl_3.6H_2O$
10 mg/l: $CuCl_2.2H_2O$
10 mg/l: $MnCl_2.4H_2O$
10 mg/l: $Na_2B_4O_7.10H_2O$
10 mg/l: $(NH_4)_6Mo_7O_{24}.4H_2O$ The suspensions obtained are centrifuged (6000 r.p.m.) under sterile conditions and resuspended in 2 ml each of medium $P_1$. To 1 ml of each suspension 1 ml of sterile lysozyme solution is added (20 mg/ml) under sterile conditions (final concentration of lysozyme is 10 mg/ml). Lysozyme itself (Calbiochem, San Diego, Calif.; 17,000 U/mg) is dissolved in medium $P_1$. The cultures containing lysozyme are slowly shaken in 25 ml Erlenmeyer flasks at 37° C. According to microscopic observations the cultures are quantitatively converted into protoplasts within 30 to 60 minutes. The protoplast suspensions obtained are centrifuged under sterile conditions, and resuspended in 2 ml each of medium $P_1$, then this operation is repeated once more.

To carry out protoplast fusion the protoplast suspension of the two different mutants is combined in a ratio of 1:1, then 0.1 ml of this suspension is left to stand for 30 minutes in 0.9 ml of 50% aqueous polyethylene glycol (m.w. 6000) containing 15% of dimethyl sulfoxide. 0.05 ml of the suspension treated with polyethylene glycol is added dropwise into soft medium $R_1$ containing 0.5% of agar. The resulting mixture is layered on solid medium $R_1$ containing 2.2% of agar. The composition of medium $R_1$ is as follows:

0.2 M: sucrose
0.25 g/l: $K_2SO_4$
1.0%: glucose
0.3%: proline
0.01%: casamino acid
2.0 ml/l: solution containing trace elements
0.025 M: TRIS-HCl buffer pH 7.5
50 mM: $MgCl_2$
10 mM: $CaCl_2$
0.2 mM: $KH_2PO_4$
0.1%: yeast extract
dissolved in distilled water.

After 20 days the colonies grown at 32° C. are washed off with a physiologic salt solution, and plated onto a medium of the following composition:
0.1%: $KNO_3$
0.05%: $K_2HPO_4$
0.05%: $MgSO_4.7H_2O$
0.05%: NaCl
0.001%: $FeSO_4.7H_2O$
2.0%: water-soluble starch
0.001%: rifampicin
1.5%: agar
dissolved in distilled water.

Following incubation of 4 to 6 days the colonies grown on this medium have genetic material which is different from that of the parent strains.

EXAMPLE 2

The deep-frozen, vegetative mycelium of the following two mutants of gentamicin-producer *Micromonospora purpurea* var. *nigrescens* (MNG 00122):
1. streptomycin resistant $Sm^R$
2. streptomycin sensitive $Sm^S$
each is inoculated under sterile conditions into 500 ml Erlenmeyer flasks containing each 100 ml of a sterile medium consisting of
1%: glucose
0.4%: peptone
0.4%: yeast extract
0.3%: glycine
0.2%: $KH_2PO_4$
0.4%: $K_2HPO_4$
0.05%: $MgSO_4.7H_2O$
2 ml/l: solution containing trace elements
dissolved in distilled water.

The cultures are incubated for 42 to 44 hours at 37° C. on a rotary shaker (320 r.p.m.). Then both cultures are centrifuged (6000 r.p.m., 0° C.) under sterile conditions, and the residue is suspended in 20 ml. of medium $P_2$ having the following composition:
0.2 M: sucrose
0.25 g/l: $K_2SO_4$
0.025 M: TRIS-HCl buffer pH 7.2
50 mM: $CaCl_2$
50 mM: $MgCl_2$
0.8 mM: $KH_2PO_4$
2 ml/l: solution containing trace elements
dissolved in distilled water.

The suspensions obtained are centrifuged (6000 r.p.m., 0° C.) under sterile conditions, and resuspended in 2 ml of medium $P_2$. To 1 ml of each suspension sterile lysozyme solution (10 mg/ml) is added (final lysozyme concentration: 5 mg/ml). The lysozyme (Calbiochem, San Diego, Calif.; 17 000 U/mg) itself is dissolved in medium $P_2$. The cultures containing lysozyme are slowly (30 r.p.m.) shaken in 25 ml Erlenmeyer flasks at 37° C. According to microscopic observations the cultures are converted quantitatively into protoplasts in about 30 to 45 minutes. The protoplast suspensions obtained are centrifuged (6000 r.p.m.) under sterile conditions. The protoplasts of the streptomycin sensitive mutant are washed twice, i.e. they are resuspended in 10 ml each of medium $R_2$ and centrifuged. This operation is repeated once more.

Composition of medium $R_2$:
0.35 M: sucrose
0.25 g/l: $K_2SO_4$
1.0%: glucose
0.3%: proline
0.01%: casamino acid
50 mM: $CaCl_2$
50 mM: $MgCl_2$
0.2 mM: $KH_2PO_4$
2 ml/l solution containing trace elements
dissolved in distilled water.

The streptomycin-resistant mutant is also washed twice with medium $P_2$ then poured into a conical 25 ml flask containing 10 ml of a TRIS medium and preheated to 55° C. Composition of the TRIS medium:
1.2%: TRIS
0.035%: KCl
0.1%: NH$_4$Cl
0.03%: MgCl$_2$.6H$_2$O
0.0058%: NaCl
0.03%: Na$_2$SO$_4$.10H$_2$O
0.5 µg/ml: FeCl$_2$
0.35 M: sucrose
dissolved in distilled water. The pH value of the medium is set to 7.5.

The flask is incubated for 3 hours at 55° C. without shaking, then the protoplasts are suspended by cautious shaking. Both the streptomycin-sensitive protoplast suspension, which did not undergo heat inactivation, and the streptomycin-resistant protoplast suspension, which received heat treatment, are combined at a ratio of 1:1. 0.1 ml of the resulting suspension is left to stand for 10 minutes in 0.9 ml of a 50% aqueous polyethylene glycol (m.w. 6000) solution. 0.05 ml of the suspension containing the fused protoplasts are added dropwise to medium R$_2$ (3 ml) containing 0.4% of agar. The mixture obtained is layered on solid medium R$_2$ containing 2.2% of agar, and subsequently incubated at 37° C. On the 8th day TRIS medium containing 10,000 µg/ml of streptomycin and 0.5% of agar (3 ml) is layered on the plates. The colonies appearing after the 20$^{th}$ day are growing as a result of protoplast fusion and subsequent recombination.

EXAMPLE 3

The protoplast fusion of the following gentamicin-producer *Micromonospora purpurea* var. nigrescens parent pair
1. casamino-acid dependent and
2. non-dependent on casamino acid
for growth is performed according to the process described in Example 2. The mutant non-dependent on casamino acid is heat-inactivated as described in Example 2 for the streptomycin-resistant mutant. The heat-inactivated protoplast suspension prepared from the prototrophic parent, and the protoplast suspension untreated by heat and prepared from the casamino-acid dependent parent, are fused according to Example 2. The resulting mixture is layered on solid medium R$_2$ containing 2.2% of agar and free from casamino acid, and incubated at 37° C. The colonies appearing after 20 to 30 days are growing as a result of protoplast fusion and subsequent recombination.

EXAMPLE 4

In order to prove the fusion between two species the following two parent pairs are applied:
1. *Micromonospora purpurea* var. nigrescens resistant to 100 µg/ml streptomycin
2. *Micromonospora inyoensis* resistant to 0.5 µg/ml streptomycin.

Heat-inactivated protoplast suspension is prepared from *Micromonospora purpurea* var. nigrescens according to Example 2. The protoplasts which received heat treatment and the protoplast suspension prepared from *Micromonospora inyoensis* according to Example 1 are combined at a ratio of 1:1, the resulting suspension is fused according to Example 1, and subsequently regenerated. On the 8th day the regenerated protoplasts are layered with 3 ml of a TRIS medium containing 1000 µg/ml of streptomycin and 0.5% of agar. The colonies appearing after the 20th day are growing as a result of protoplast fusion between the two species and their subsequent recombination.

What we claim is:
1. A process for preparing an antibiotic-producing Micromonospora strain having modified genetic material, which comprises preparing, following cultivation in a glycine medium, a protoplast suspension of each of two genetically different mutants of antibiotic-producing Micromonospora with lysozyme, under osmotically buffered conditions ensured by sucrose, combining the two suspensions thus obtained in the presence of polyethylene glycol, incubating at room temperature, suspending the resulting fused protoplasts in soft agar, then plating the suspended protoplasts on an agar plate containing sucrose, proline and inorganic salts, incubating the plated protoplasts for 20 to 30 days, selecting all colonies from the regenerated colonies which are sure to have genetic material different from that of said two mutants, and, prior to fusion, heat-inactivating the protoplasts of one of said mutants by heating them at 55° C. for three hours, thereby to permit the genetic material of the non-heated protoplasts to be transferred into the cytoplasm of the heat-inactivated protoplasts.

2. A process as claimed in claim 1, characterized in that the protoplasts are prepared from cultures being at the beginning of their logarithmic growth phase.

3. A process as claimed in claim 1, characterized in that the transfer of genetic information is carried out within a species.

4. A process as claimed in claim 3, characterized in that sisomicin-producer *Micromonospora inyoensis* strain is used.

5. A process as claimed in claim 3, characterized in that gentamicin-producer *Micromonospora purpurea* var. nigrescens strain is used.

6. A process as claimed in claim 3, characterized in that gentamicin-producer *Micromonospora purpurea* (holotype) is used.

7. A process as claimed in claim 3, characterized in that gentamicin-producer *Micromonospora echinospora* strain is used.

8. A process as claimed in claim 3, characterized in that fortimicin-producer *Micromonospora olivoasterospora* strain is used.

9. A process as claimed in claim 1, characterized in that the transfer of genetic information is carried out between two species.

* * * * *